United States Patent [19]

Manahan, Sr.

[11] Patent Number: 5,641,912

[45] Date of Patent: Jun. 24, 1997

[54] METHOD FOR REMOTE APPLICATION OF VARIABLE LOAD AND/OR DISPLACEMENT TO SPECIMENS, COMPONENTS, OR SYSTEMS

[76] Inventor: Michael Peter Manahan, Sr., 213 Teaberry Cir., State College, Pa. 16803-1269

[21] Appl. No.: 358,409

[22] Filed: Dec. 19, 1994

Related U.S. Application Data

[63] Continuation-in-part of Ser. No. 12,244, Feb. 1, 1993, abandoned.
[51] Int. Cl.$^6$ .................................................. G01N 3/18
[52] U.S. Cl. ...................... 73/797; 73/798; 73/799; 73/804; 73/818; 73/825; 73/826; 73/837; 73/857; 374/50; 374/51
[58] Field of Search .................... 73/804, 825, 837, 73/790, 795, 796, 797, 799, 798, 826, 818, 857; 374/50, 51

[56] References Cited

FOREIGN PATENT DOCUMENTS

| 1295275 | 3/1987 | U.S.S.R. | 73/825 |
| 1345095 | 10/1987 | U.S.S.R. | 73/825 |
| 1698686 | 12/1991 | U.S.S.R. | 73/826 |

*Primary Examiner*—Hezron E. Williams
*Assistant Examiner*—Nashmiya Ashraf

[57] ABSTRACT

A method and apparatus for applying a force, displacement, or both to specimens, components, or systems by using a remote variable load/deflection device. The method enables testing of materials under actual in-service conditions. A displaceable container with a heating or heating and cooling element inside is provided. As heat is applied to the element, it expands thermally and causes the container to displace and apply force to specimens, components, or systems. The load/displacement of the container is modified by heating or cooling the element material. The container may be attached to in-service specimens, components, or systems and used to study the material behavior during in-service operation.

18 Claims, 6 Drawing Sheets

METHOD FOR REMOTE APPLICATION OF VARIABLE LOAD AND/OR DISPLACEMENT TO SPECIMENS, COMPONENTS, OR SYSTEMS

This is a continuation-in-part of Ser. No. 08/012,244, filed on Feb. 1, 1993, now abandoned. The continuation-in-part was filed on Dec. 19, 1994, entitled, "Method for Remote Application of Variable Load and/or Displacement to Specimens, Components, or Systems". The Amendment to the CIP was filed on Sep. 18, 1996.

FIELD OF INVENTION

This invention relates to methods and apparatus for application of forces (loads), displacements, or forces and displacements to specimens, components, or systems, and is especially useful for determining and measuring the behavior of materials in hostile environments when loaded, displaced, or both for the purpose of establishing the design, use, and safe life criteria of the material.

In many applications, the method must be employed in conjunction with miniature specimens to accommodate in-service system space constraints, and the loading/ displacement apparatus must itself be miniaturized. Although the term "miniature" is relative, as are all size descriptive terms, it is a fair characterization to define the field of this invention as the application of load, displacement, or both to specimens, components, or systems using conventionally sized or miniaturized remote variable load/displacement apparatus where, miniature means noticeably smaller than prior conventional remote variable load/ displacement apparatus. The primary intended use involves remote application of load, displacement, or both to specimens since the device may be placed in hostile environments where human life would be threatened or where size constraints would preclude direct access to the apparatus during operation. An example is the placement of the apparatus in the core of a nuclear power plant attached to a miniaturized double cantilever beam specimen for measurement of crack growth rate during plant operation. In this context, remote refers to the placement of the apparatus in a place where visual observation and control is difficult or impossible. While use of the apparatus in conventional laboratory or in non-nuclear field applications is not precluded, it is likely that conventional load/displacement devices would be more appropriate in such cases.

BACKGROUND OF THE INVENTION

Determination of the mechanical behavior and physical properties of materials is necessary so that materials may be selected for use, evaluated when in use, and evaluated after use. From these determinations, decisions are made as to which materials to use, the conditions under which they can be used, and whether such materials in use can be continued to be used with safety. These types of determinations are particularly useful for determining the effects of environmental loading such as nuclear radiation, temperature, water chemistry, and force on the mechanical properties of in-service materials.

While not limited to the field of determining the effects of nuclear irradiation and environment on the mechanical properties of materials, the impetus for the invention originated with the needs and necessities of this activity. The invention is fully applicable to the determination of mechanical behavior of materials not subjected to radiation, and the validity of the invention was demonstrated for materials not subjected to radiation.

In the past, the most common procedure has been to determine the mechanical behavior of a material by testing large samples that are created more or less simultaneously or "side by side" with the product that is intended to be used. In determination of the mechanical behavior of solid materials, and particularly metals, the practice is to make tensile, stress-corrosion cracking, S-N fatigue, creep, stress relaxation, ductile/brittle transition, compact tension, fracture mechanics, fatigue crack initiation/propagation, fracture modes, fracture stress/strain, multilayered, residual plastic stress/strain, ion irradiated, etc. specimens, and these are then subjected to forces, displacements, or both using conventional screw driven or servohydraulic testing machines while measurements are taken of the force, time, displacement, impact energy decrement, velocity, crack propagation, etc. of the specimen. Information such as stress and strain, which can be thought of as normalized load and deflection respectively, and crack length are then obtained by simple mathematical operations and previous calibrations. For example, in a uniaxial tensile test, the stress is determined by dividing the measured load by the specimen cross sectional area. In a fracture mechanics test, the crack extension is determined by visual examination, or by the electric potential method, or the unloading compliance method, or any combination of these methods.

While the common procedure to determine mechanical behavior of materials may be satisfactory in some instances, there are other circumstances where it is desirable to load, displace, or both load and displace specimens in a hostile environment using remotely controlled load, displacement, or both load and displacement. This approach is particularly effective in characterizing the phenomenon of corrosive attack, such as stress-corrosion cracking (SCC). When studying SCC in the laboratory, it is often difficult to simulate the actual in-service environment. Thus, it is of great importance to be able to load, displace, or both load and displace specimens, components, and systems remotely during actual in-service operation.

The present invention was conceived as a solution to the problem of determining SCC behavior in power plants during full power operation. There are five principal conceptual innovative aspects to the method for remote application of load, displacement, or both to specimens, components, or systems. The first is the use of an expandable, contractible, or both expandable and contractible (displaceable) container with a heating or heating and cooling element capable of heating or heating and cooling a solid material inside the container. The second is the use of a solid material force/displacement exerting member, of sufficient size to contact ends of the container, inside the container which is capable of expanding upon heating, contracting upon cooling, or both. The third is to modify the load exerted by the container, to modify the displacement of the container, or both by heating or heating and cooling the element and solid force/displacement exerting expansion/ contraction material. This process results in the expansion or contraction of the container. The fourth is to attach the container to the specimen, component, or system and to apply load, deflection, or both. The fifth is to modify the heating or heating and cooling applied to the force/ displacement exerting member in a controlled manner to obtain a desired load, deflection, or both.

There are several important advantages of the invention described here over the approach which uses fluid pressurization to expand a bellows. The first is that only solid wire penetrations of the nuclear reactor primary system are needed for the electrically heated solid material variable load system to function. Fluid carrying penetrations present a more direct threat to depressurizing the reactor coolant system during operation. Another important advantage of the solid material force/displacement exerting invention is that active valves are not required to equalize displacement during nuclear reactor plant startups or transients. Another advantage of the solid material force/displacement exerting invention is the superior load/displacement control which can be achieved as compared to fluid systems which experience longer feedback effects and instability due to fluid boiling.

SUMMARY OF THE INVENTION

In summary, the remote variable load/deflection invention is:

1. An apparatus for providing a force, a displacement, or both a force and a displacement, comprising:
   a. a displaceable container (101) with a heating element (137) capable of heating a force/displacement exerting member (105) of solid material of sufficient size to contact ends of the container;
   b. said solid material force/displacement exerting member, which is capable of expanding upon heating and contracting upon cooling, being located inside said container;
   c. said heating element comprising electrical resistance wire (132) inside electrical insulation material (131); and
   d. means for heating said element which in turn heats said force/displacement exerting member, which results in an expansion of the force/displacement exerting member, which displaces the container, induces a force, or both displaces the container and induces a force.

2. An apparatus for providing a force, a displacement, or both a force and a displacement, comprising:
   a. a displaceable container (101) with a heating element capable of exerting force/displacement (135) of sufficient size to contact ends of the container;
   b. said heating element, which is capable of expanding upon heating and contracting upon cooling, being located inside said container;
   c. electrical insulation (131) inside said container which is capable of electrically insulating said heating element;
   d. said heating element comprising a material which heats when electric current flows through said heating element; and
   e. means for heating said element, which in turn expands element, which in turn causes application of a force by the container, a displacement of the container, or both a force by and a displacement of the container.

3. An apparatus for providing a force, a displacement, or both a force and a displacement, comprising:
   a. a displaceable container (101) with a heating element capable of exerting force/displacement (135) of sufficient size to contact ends of the container and which is capable of expansion upon heating or contraction upon cooling;
   b. said heating element comprising a material which expands on heating and contracts on cooling and which contains fluid lines (133) which allow fluid to pass through the element for the purpose of changing the temperature of the element; and
   c. means for heating or cooling said element, which in turn expands or contracts, which in turn causes application of a force by the container, a displacement of the container, or both a force by and a displacement of the container.

4. A process of providing a force, a displacement, or both a force and a displacement, comprising:
   a. providing a displaceable container (101) with a heating element (137) capable of heating a force/displacement exerting member (105) of solid material of sufficient size to contact ends of the container;
   b. providing said solid material force/displacement exerting member, which is capable of expanding upon heating and contracting upon cooling, for placement inside said container;
   c. providing said heating element comprising electrical resistance wire (132) inside electrical insulation (131); and
   d. heating said element which in turn heats said force/displacement exerting member, which results in an expansion of the force/displacement exerting member, which displaces the container, induces a force, or both displaces the container and induces a force.

5. A process of providing a force, a displacement, or both a force and a displacement, comprising:
   a. providing a displaceable container (101) with a heating element capable of exerting force/displacement (135) of sufficient size to contact ends of the container;
   b. providing said heating element which is capable of expanding upon heating and contracting upon cooling, inside said container;
   c. providing electrical insulation (131) for placement inside said container which is capable of electrically insulating said heating element;
   d. providing said heating element comprising a material which heats when electric current flows through said heating element; and
   e. heating said element, which in turn expands element, which in turn causes application of a force by the container, a displacement of the container, or both a force by and a displacement of the container.

6. A process of providing a force, a displacement, or both a force and a displacement, comprising;
   a. providing a displaceable container (101) with a heating element capable of exerting force/displacement (135) of sufficient size to contact ends of the container and which is capable of expansion upon heating or contraction upon cooling;
   b. providing said heating element comprising a material which expands on heating and contracts on cooling and which contains fluid lines (133) which allow fluid to pass through the element for the purpose of changing the temperature of the element; and
   c. heating or cooling said element, which in turn expands or contracts, which in turn causes application of a force by the container, a displacement of the container, or both a force by and a displacement of the container.

An object of this invention is to provide force, displacement, or both to specimens, components, and systems in-service during facility operation. This novel approach enables testing and characterization of in-service materials and systems remotely in the actual in-service environment. A particular application is the study of stress-corrosion cracking in power plants. In-service measurements can be made using the process described herein by attaching the remote variable load/deflection device to a double cantilever beam specimen and measuring the crack extension as a function of applied load/deflection and time.

Another application is performing various mechanical behavior tests (such as tensile, fracture toughness, creep, fatigue, notch toughness) in hostile environments such as high temperature, radiation field, high velocity as on aircraft, and in chemical environments. In cases where space is limited, the remote variable load/displacement device can be miniaturized.

An overall object of the invention is to provide remote variable loads, displacements, or both to specimens, components, and systems.

Other objects and features of this invention are apparent from the detailed description of the invention and the accompanying drawings which follow. The foregoing and other advantages of the invention will become apparent from the following disclosure in which a preferred embodiment of the invention is described in detail and illustrated in the accompanying drawings. It is contemplated that variations in structural features and arrangement of parts may appear to the person skilled in the art, without departing from the scope or sacrificing any of the advantages of the invention.

REFERENCE NUMERALS IN DRAWINGS

| 101 | displaceable container |
|---|---|
| 102, 103 | end caps |
| 104 | inner volume |
| 105 | force/displacement exerting member |
| 106 | insulated electric current conducting wires |
| 107 | external thermal insulation/guide cylinder |
| 108 | internal thermal insulation |
| 109 | attachment |
| 114 | load cell |
| 115 | double cantilever beam specimen |
| 116, 117 | external thermal insulation |
| 122 | thermocouple |
| 123 | linear variable displacement transducer (LVDT) |
| 131 | electrical insulation |
| 132 | electrical resistance wire |
| 133 | fluid lines |
| 134 | bare conducting wire |
| 135 | heating element capable of exerting force/displacement |
| 136 | refractory material |
| 137 | heating element. |

DETAILED DESCRIPTION OF THE INVENTION AND BEST MODE FOR CARRYING OUT THE PREFERRED EMBODIMENT

Figure 1:
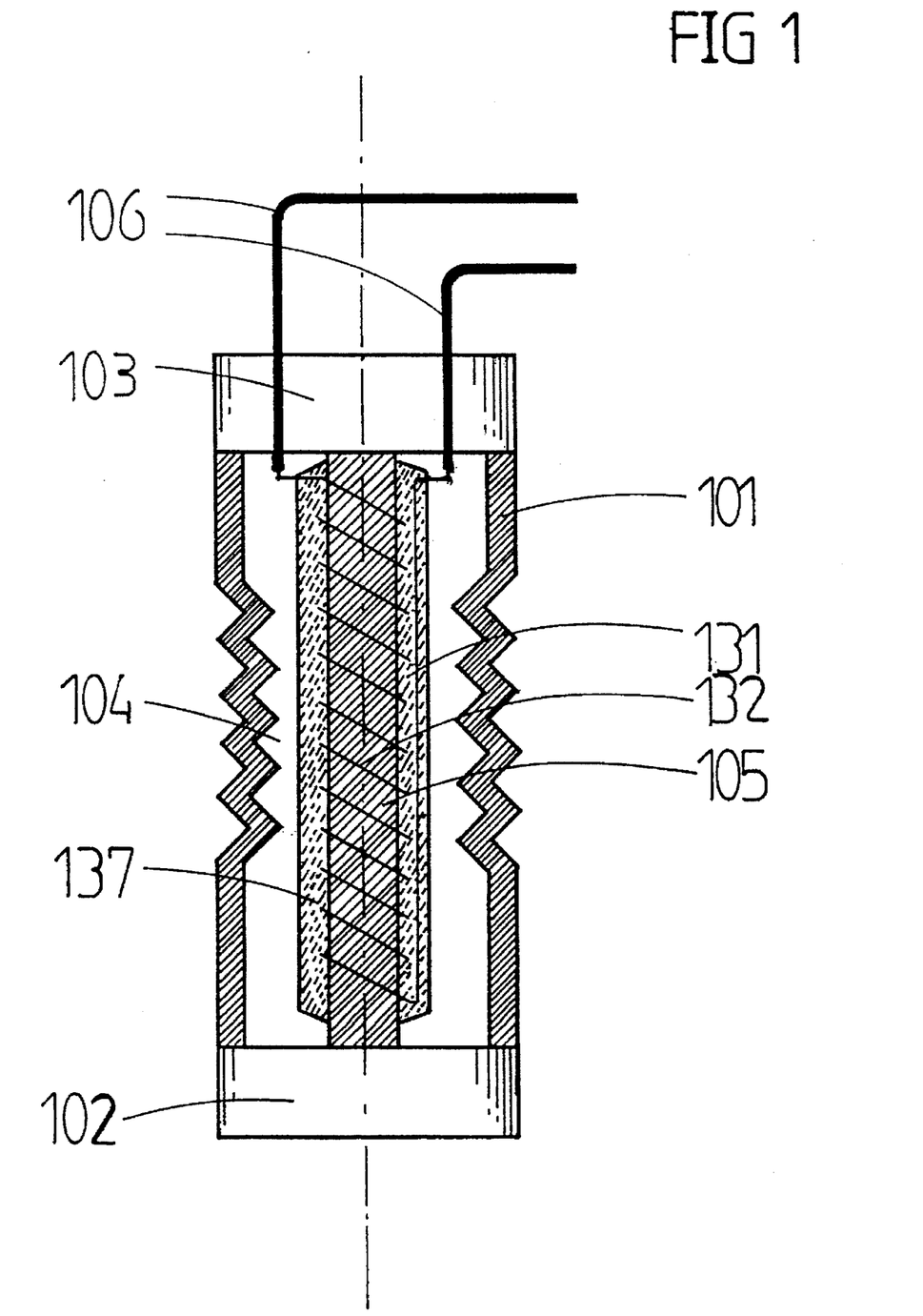
FIG. 1 is a schematic sectional elevational view of the variable load/displacement device with an electrical resistance wire (132) wound around the force/displacement exerting member (105) which causes the displaceable container (101) to expand when the member (105) is heated.

Referring to FIG. 1, a typical process according to this invention is carried out using a displaceable container 101 (expandable, contractible, or both expandable and contractible) with an internal solid material force/displacement exerting member 105 which is heated using a heating element (137). Inner volume 104 can be vacuum, thermal insulation, or both. The end caps (102, 103) are welded or otherwise attached to ensure complete sealing of the container. The container (101, plus 102, plus 103) form a sealed volume. Insulated electric current conducting wires 106 provide current to electrical resistance wire 132 which heats when current flows. An example resistance material (132) is Nichrome. Electrical insulation 131 keeps the electrical resistance wire electrically isolated. The use of high temperature electrical insulators such as refractory materials are preferred for this application. An example of electrical insulation (131) material is alumina. For high deflection applications, it is preferable to match the coefficient of the thermal expansion (CTE) of the electrical insulator (131) with the CTE of the member 105 as closely as possible. When the resistance wire (132) heats, the heat is transferred to the insulator (131) which heats and transfers heat to the force/displacement exerting member (105) which heats and thermally expands. The member exerts force, displacement, or both on the container (101) which may be attached to a specimen, component, or system. The container (101) may be designed with sufficient stiffness so that the end caps (102, 103) are in rigid contact with the force/displacement exerting member. This is accomplished by welding the end caps in position with the load train pretensioned. The container (101) may be designed so that it is expandable only. This may be accomplished by expanding the bellows so that it undergoes plastic deformation and then welding the end caps (102, 103) onto the bellows so that they are in rigid contact with the force/displacement exerting member. Each increment of temperature increase of the force/displacement exerting member results in further permanent expansion of the container. If the temperature of the force/displacement exerting member is decreased, the container will not decrease its deflection because of plasticity effects. The container (101) may be designed so that it is contractible only. This may be accomplished by heating the force/displacement exerting member to its maximum achievable deflection, mechanically expanding the bellows to a deflection below yielding, and welding the end caps onto the bellows. After the welding is completed and the container is attached to a mechanical specimen, the heating of the force/displacement exerting member may be terminated and the force/displacement exerting member allowed to cool thus resulting in a contractible only container. The container (101) may also be designed so that it is both expandable and contractible. This may be accomplished by expanding the bellows to a deflection within its elastic range and welding the end caps onto the bellows. The container will expand if the force/displacement exerting member is heated and the container will contract if the temperature of the force/displacement exerting member is decreased.

Figure 2:
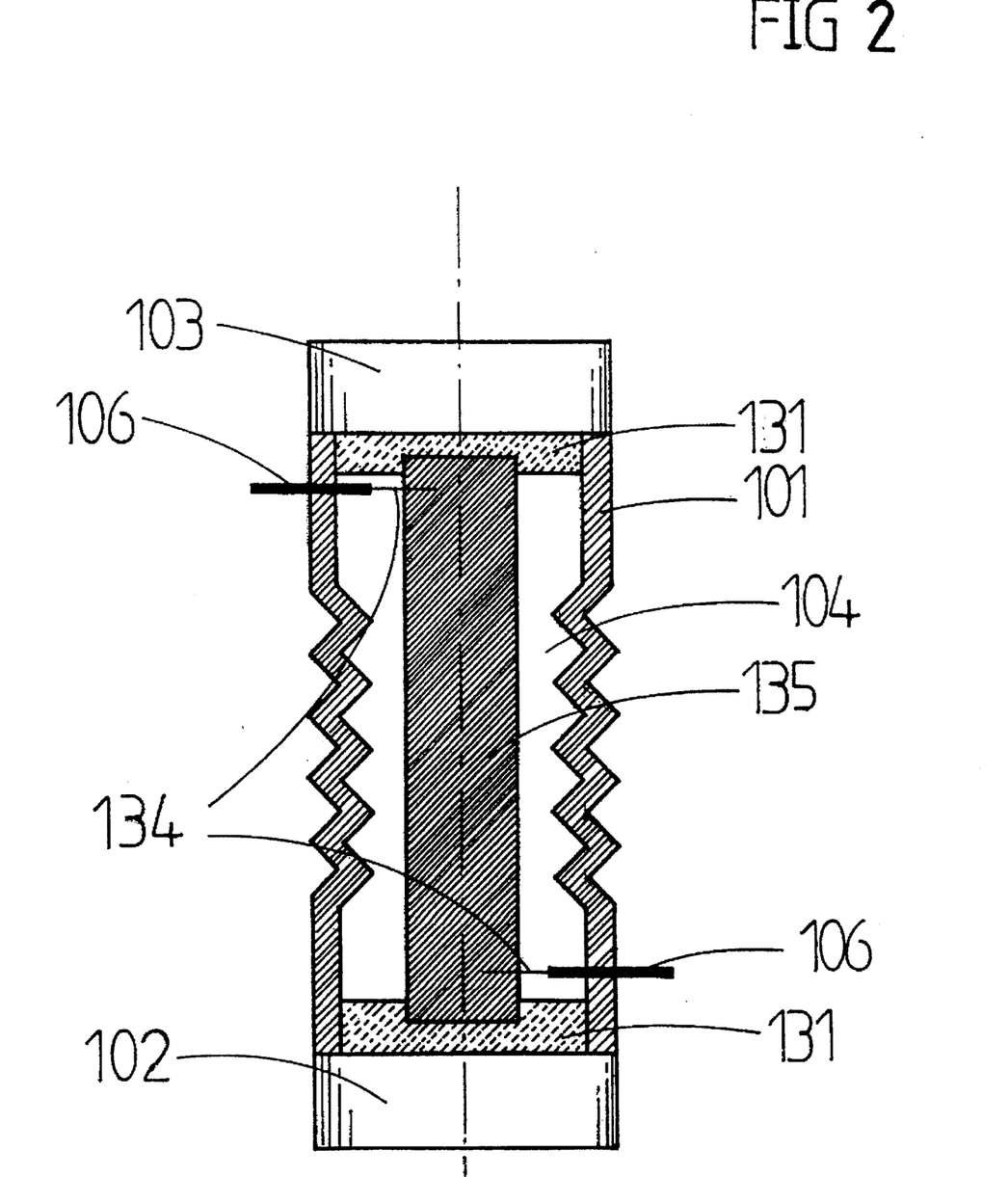
FIG. 2 is a schematic sectional elevational view of the variable load/displacement device with the heating element (135) expansion controlled by the mount of current which passes through the element. When electrical current passes through the electrically resistive element (135), the element expands thermally and causes the container (101) to displace, load, or both displace and load a specimen, component, or system.

Referring to FIG. 2, it is seen that it is possible to preclude the need for a separate force/displacement exerting member (105 in FIG. 1) by providing a heating element capable of exerting force/displacement 135. In a typical preferred embodiment, the element (135) is comprised of electrical resistance material such as Nichrome and the element is in contact with an electrical insulation (131) which may be comprised of a refractory material. As shown in FIG. 2, the element (135) is connected to the insulated conducting wires (106) through bare conducting wires 134.

Figure 3:
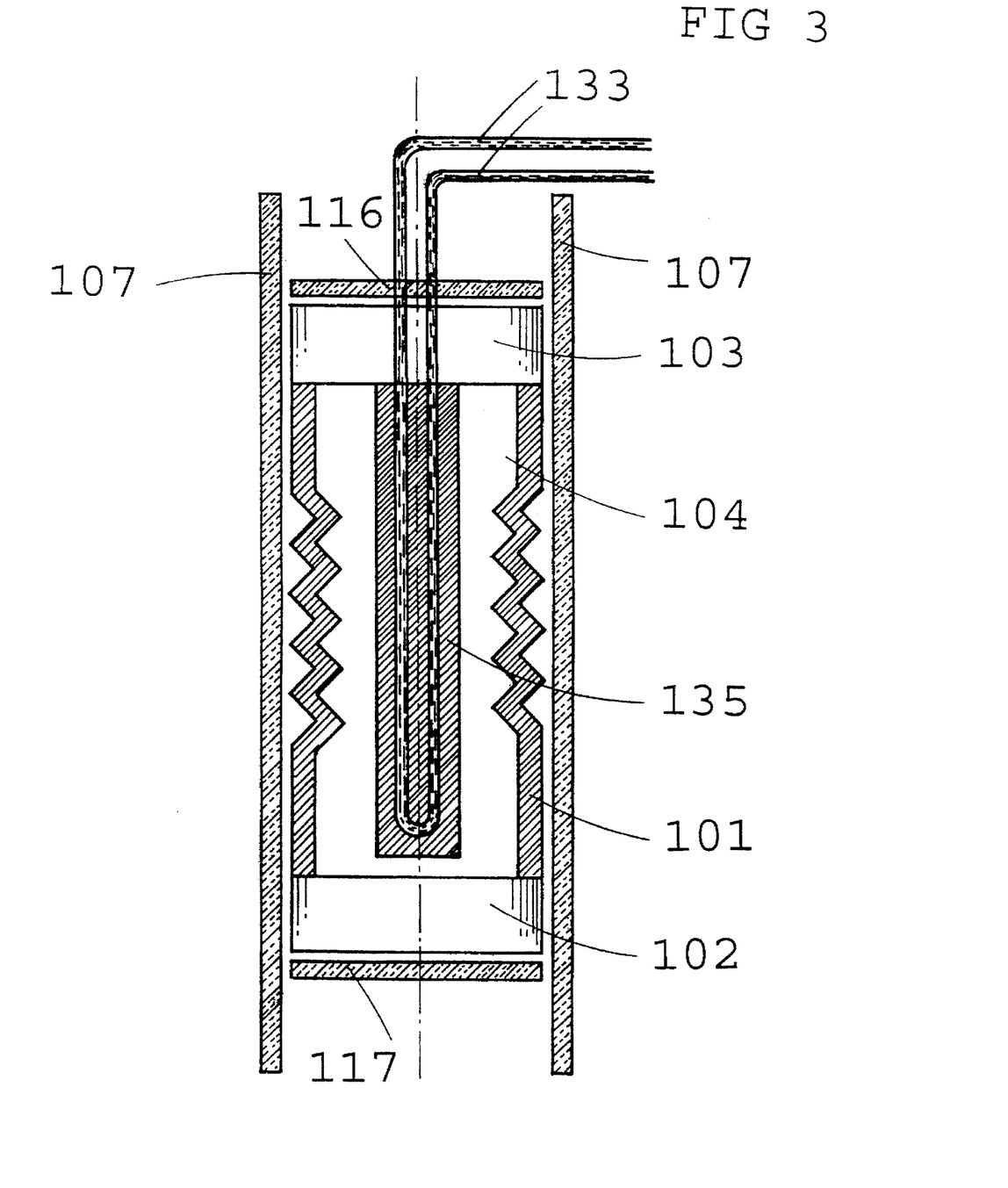
FIG. 3 is a schematic sectional elevational view of the variable load/displacement device with external thermal insulation (107, 116, 117) and guide cylinder (107) for applications where there is large heat loss or the container (101) tilts on expansion, or contraction, or both. The fluid lines (133) carry fluid (liquid or gas) which transfers heat to the heating element capable of exerting force/displacement (135) which in turn expands or contracts the container (101).

Referring to FIG. 3, the heating and/or cooling element capable of exerting force/displacement (135) may be heated and/or cooled using fluid lines 133. The fluid is heated or cooled outside the container. The thermally conditioned fluid flows through the fluid lines into the container (101) and transfers heat to the element (135). When the solid material is heated, it expands, and when it is cooled, it contracts. The fluid is kept separated from the container inside volume (104) since the fluid lines are a sealed volume relative to the container. In cases where heat loss to the environment outside the container is significant, external thermal insulation (107, 116, 117) may be provided around the outside surface of the container (101). In cases where a container with low stiffness is used, an external thermal insulation/guide cylinder 107 may act as a displacement guide.

In a preferred embodiment, referring to FIG. 1, the container (101) is shaped in the form of a uniaxial bellows and is fabricated from metal such as stainless steel, the end caps 102, 103 are fabricated from a weld compatible material such as stainless steel, the inner volume 104 is vacuum, the solid material member 105 is a cylinder of high CTE stainless steel and is heated by an electrical resistance wire (132) coiled around and embedded in a high expansion coefficient refractory material (131), and the electrical current for the heater is carried by insulated wires 106.

In another embodiment, referring to FIG. 2, the container (101) is shaped in the form of a uniaxial bellows and is fabricated from metal such as stainless steel, the end caps 102, 103 are fabricated from a material which can be welded to stainless steel, the region 104 is vacuum, the element 135 is a material such as Nichrome which heats and expands when electric current flows through it, the electric current is carried by wires 106, and the electrical insulators 131 are high density alumina discs which also provide thermal insulation.

Referring to FIG. 3, insulation (107, 116, 117) can be placed around the container 101 and the end caps (102, 103) to minimize heat loss to the surrounding environment. The need for insulation depends on the conductivity of the element 135, the thermal insulation characteristics of inner volume 104, and container 101 and the heat transfer coefficient between the container and the surrounding environment. Minimizing the heat loss enables a greater maximum deflection and applied load, and provides greater temperature control sensitivity.

Figure 4:
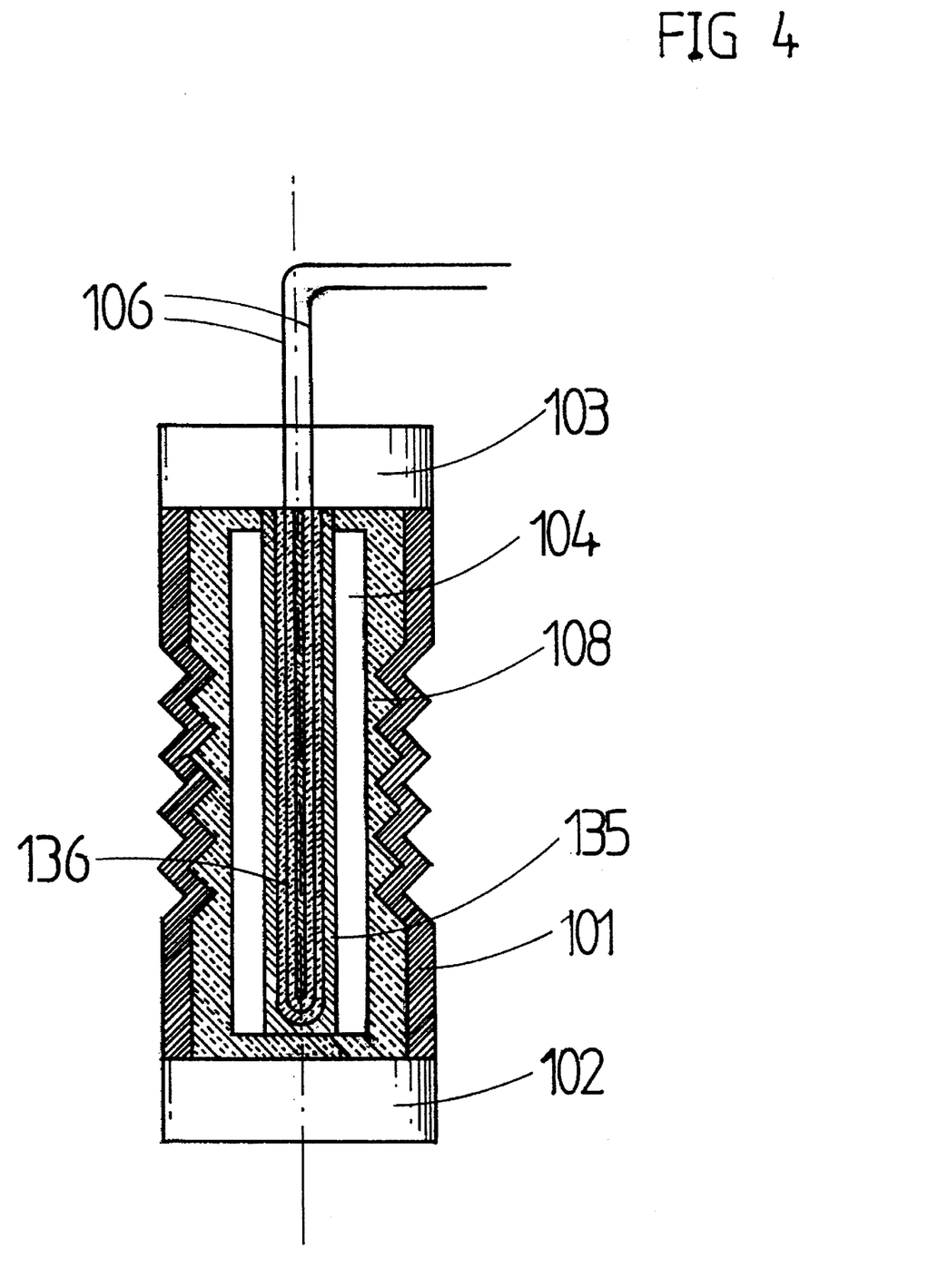
FIG. 4 is a schematic sectional elevational view of the variable load/displacement device with internal thermal insulation (108) for applications where there is large heat loss. The conducting wires (106) deliver electrical current to the electrical resistance wire surrounded by refractory material (136) which heats the force/displacement heating element (135) which in turn expands the container (101).

Referring to FIG. 4, internal thermal insulation 108 can be applied to the inside of the container 101. This approach has the advantage in some applications of ensuring compatibility of materials with the in-service environment. In another typical embodiment shown in FIG. 4, the heating element capable of exerting force/displacement (135) may be constructed using resistance wire embedded in refractory material 136 which is embedded inside the element (135).

Figure 5:
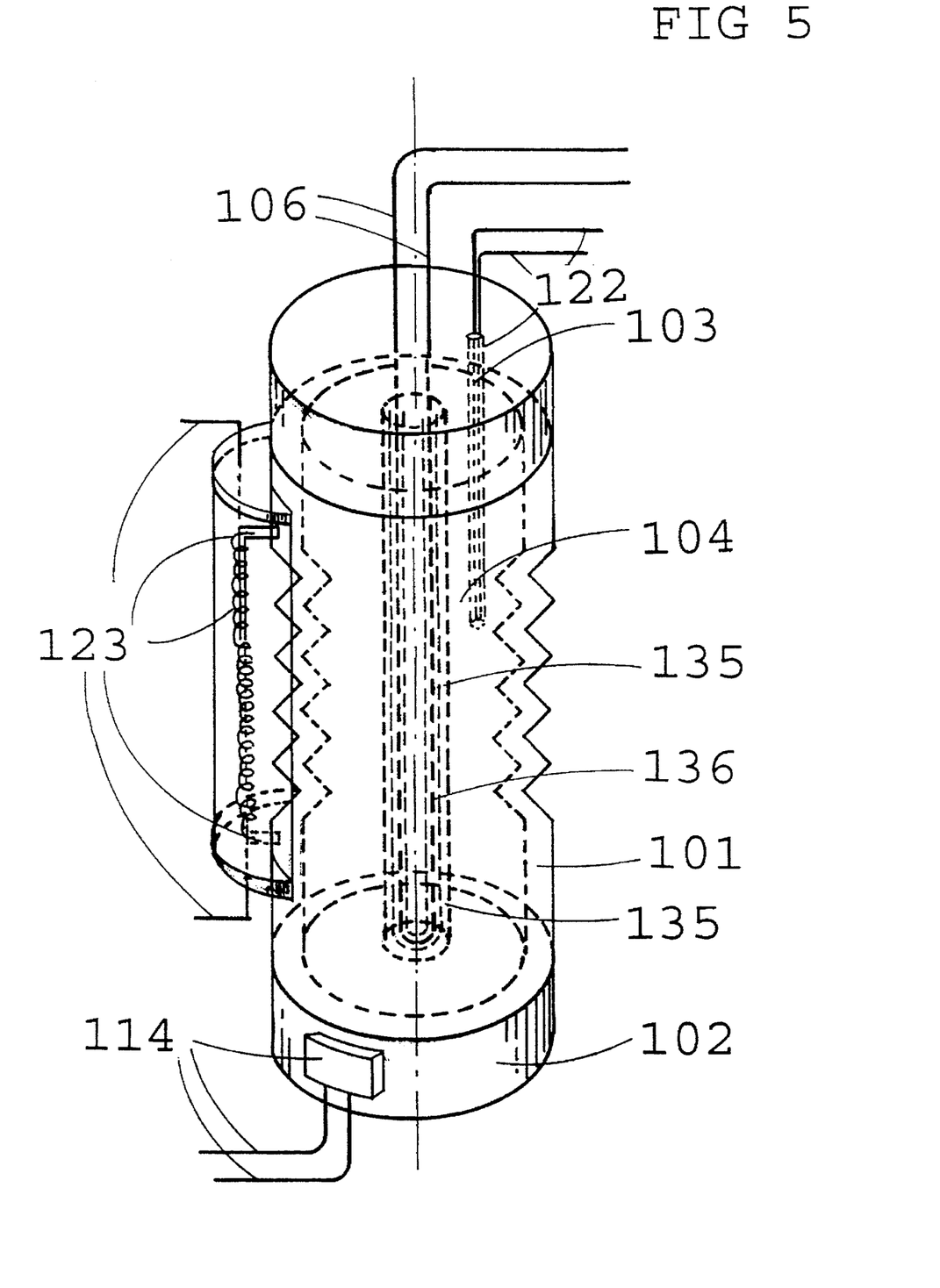
FIG. 5 is a schematic perspective view of the remote variable load/displacement device. A load cell (114) is used to measure the applied load directly and a linear variable displacement transducer (LVDT) (123) is used to measure displacement directly. A thermocouple (122) may be used to measure the temperature of the container inner volume (104). The thermocouple or additional thermocouples may be attached to the element (135), the end caps (102, 103), or to the container (101).

Referring to FIG. 5, if it is desired to measure the applied force, a load cell 114, which consists of a calibrated piezoresistance strain gage, can be attached to the container inside, outside, or both surfaces. The load cell bridge consists of strain gages attached to the surface of the container. As the container is strained under applied load, the strain gages yield a voltage change which can be calibrated. An optional linear variable displacement transducer (LVDT) 123 may be attached to the outside or inside surface of the container. The LVDT may be mechanically attached, glued, or welded in place. The LVDT must be attached such that the LVDT coil is on one side of the bellows region and the LVDT rod is on the other. A thermocouple 122 may used to measure the solid material 135, the region 104, container 101 temperature, or any combination of these temperatures.

Figure 6:
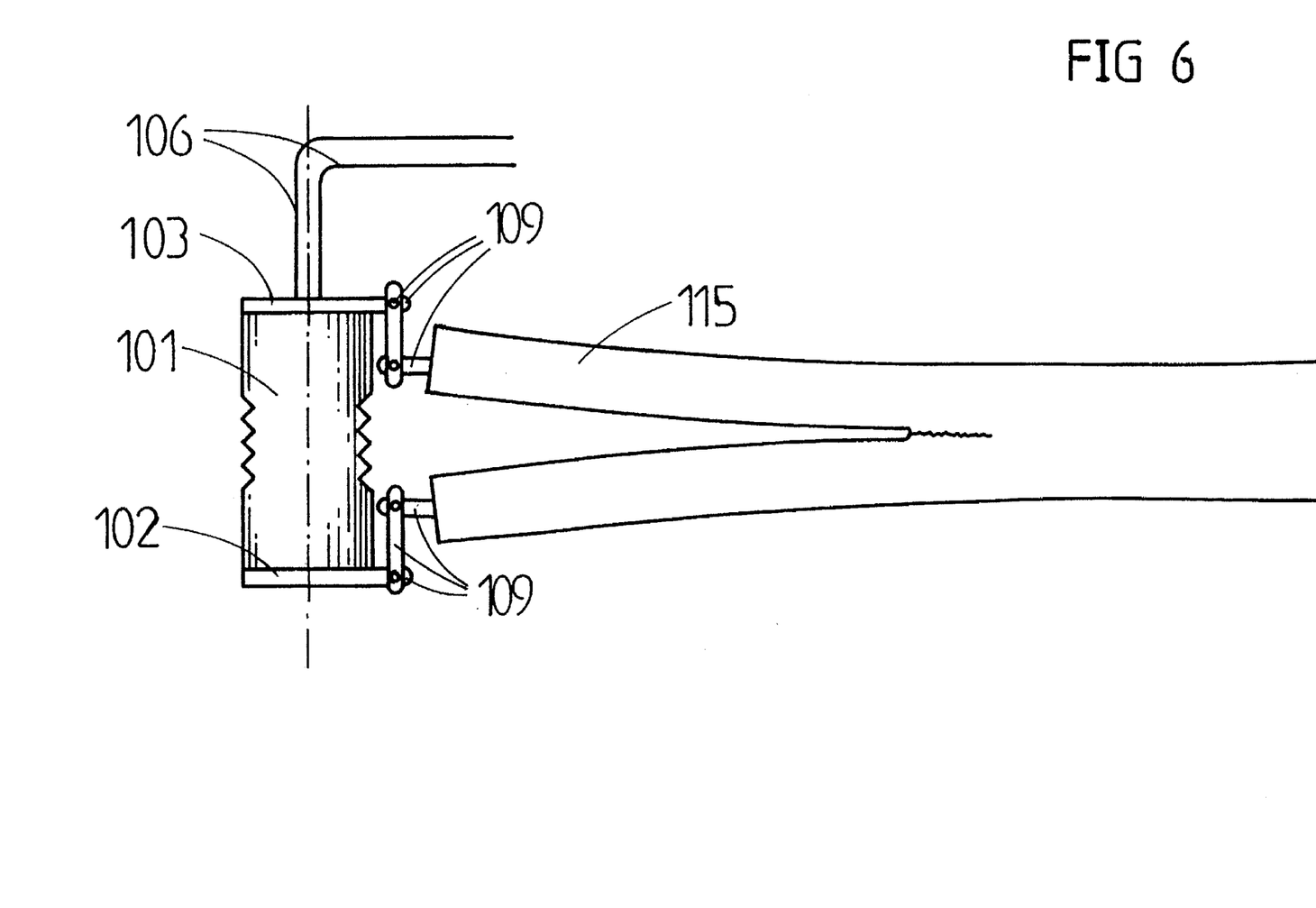
FIG. 6 is a schematic elevational view of the remote variable load/displacement device attached to a double cantilever beam specimen (115)

Referring to FIG. 6, the remote variable load device may be attached to specimens, components, or systems so that loads, deflections, or both can be applied. In a preferred embodiment, the container is provided with an attachment 109 to a double cantilever beam specimen 115. The attachment may consist of, for example, pinned joints, gears, or screw threads which are welded or otherwise attached to the load device and the specimen.

In a typical preferred embodiment of the practice of the invention, results have been obtained which demonstrate the efficacy and accuracy of the method.

Analytical Treatment

Attaching a linear viable displacement transducer (LVDT) to be container enables direct measurement of the displacement of the container as the element temperature, the member temperature, the temperature of the region inside the container, the container temperature, or any combination is varied. Attaching a load cell to the container enables direct measurement of the applied load as the heater element temperature, the temperature of the region between the element and container, or the container temperature, or any combination, is varied. In some applications, such as in a high temperature or radiation environment, it is often simpler to avoid the use of a load cell or LVDT to preclude the necessity of temperature compensating or radiation hardening the load cell, LVDT, or both. In such cases, mechanics equations exist or can be developed which enable the applied load to be calculated given the displacement of the container. The displacement of the container is In turn determined by calibrating the displacement of the container as a function of the temperature of the element, the member temperature, the temperature of the region inside the container, container temperature, or any combination. Thus, the attachment of a thermocouple to the element member, region inside the container, or container, or any combination, greatly simplifies the design and enables use of the remote variable load/deflection device in environments for which the use of load cells and LVDT is not feasible, or even impossible.

For the case of a double cantilever beam specimen, there are several relations available in the open literature. Kanninen has developed a relation between the stress intensity factor and applied load, and between load and displacement. These equations can be adapted to yield:

Relation Between Displacement (D) and Applied Load (P)

$$P = \frac{EBh^3}{4a^3 \left(1 + 1.92\frac{h}{a} + 1.22\frac{h^2}{a^2} + 0.39\frac{h^3}{a^3}\right)} D$$

where,
P is applied load (lb)
D is the arm or container displacement (inch)
a is crack length (inch)
B is the width of the specimen (inch)
h is the single arm height (inch)
E is Young's modulus (psi)

Relation Between Applied Load (P) and Stress Intensity Factor ($K_I$)

$$K_I = \frac{2\sqrt{3}\, a \left(1 + 0.64\frac{h}{a}\right)}{Bh^{3/2}} P$$

where, $K_I$ is the stress intensity factor (psi(in)$^{0.5}$)

Relation Between Displacement (D) and Stress Intensity Factor ($K_I$)

$$K_I = \frac{\sqrt{3}}{2} \frac{Eh^{3/2}}{a^2} \left(\frac{1 + 0.64\frac{h}{a}}{1 + 1.92\frac{h}{a} + 1.22\frac{h^2}{a^2} + 0.39\frac{h^3}{a^3}}\right) D$$

Calibration Approach

The remote variable load device is calibrated prior to use in a controlled load, displacement, or both, application. In the current described application of stress-corrosion cracking characterization, the container may be placed in the load train of a fully calibrated servohydraulic test machine between, for example, between two flat plates with the container axis of symmetry coincident with the direction of motion of the machine actuator. A thermocouple attached to the member or element may be used to indicate the average temperature. A relationship between container temperature and deflection, load, or both, may be established. The relationship may then be used to control the $K_I$ applied to the double cantilever beam specimen.

Best Mode

1. An apparatus for providing a force, a displacement, or both a force and a displacement, comprising:
    a. a displaceable container (101) with a heating element (137) capable of heating a force/displacement exerting member (105) of solid material of sufficient size to contact ends of the container;
    b. said solid material force/displacement exerting member, which is capable of expanding upon heating and contracting upon cooling, being located inside said container;
    c. said heating element comprising electrical resistance wire (132) inside electrical insulation material (131); and
    d. means for heating said element which in turn heats said force/displacement exerting member, which results in an expansion of the force/displacement exerting member, which displaces the container, induces a force, or both displaces the container and induces a force.

2. An apparatus for providing a force, a displacement, or both a force and a displacement, comprising:
    a. a displaceable container (101) with a heating element capable of exerting force/displacement (135) of sufficient size to contact ends of the container;
    b. said heating element, which is capable of expanding upon heating and contracting upon cooling, being located inside said container;
    c. electrical insulation (131) inside said container which is capable of electrically insulating said heating element;
    d. said heating element comprising a material which heats when electric current flows through said heating element; and
    e. means for heating said element, which in turns expands element, which in turn causes application of a force by the container, a displacement of the container, or both a force by and a displacement of the container.

3. An apparatus for providing a force, a displacement, or both a force and a displacement, comprising:
    a. a displaceable container (101) with a heating element capable of exerting force/displacement (135) of sufficient size to contact ends of the container and which is capable of expansion upon heating or contraction upon cooling;
    b. said heating element comprising a material which expands on heating and contracts on cooling and which contains fluid lines (133) which allow fluid to pass through the element for the purpose of changing the temperature of the element; and
    c. means for heating or cooling said element, which in turn expands or contracts, which in turn causes application of a force by the container, a displacement of the container, or both a force by and a displacement of the container.

4. An apparatus according to 1, 2, or 3 wherein the displaceable container (101) is in the form of a bellows.

5. An apparatus according to 1, or 2, or 3 wherein the heating element material has a large coefficient of thermal expansion.

6. An apparatus according to 1, wherein the force/displacement exerting member (105) consists of metal, polymer, organic, ceramic, or any other solid material which expands on heating and contracts on cooling.

7. An apparatus according to 1, 2, or 3 wherein thermal insulation is provided around the outside of the container, around the inside of the container, or the container is fabricated using a material which resists heat flow.

8. A process of providing a force, a displacement, or both a force and a displacement, comprising:
    a. providing a displaceable container (101) with a heating element (137) capable of healing a force/displacement exerting member (105) of solid material of sufficient size to contact ends of the container;
    b. providing said solid material force/displacement exerting member, which is capable of expanding upon heating and contracting upon cooling, for placement inside said container;
    c. providing said heating element comprising electrical resistance wire (132) inside electrical insulation (131); and d. heating said element which in turn heats said force/displacement exerting member, which results in an expansion of the force/displacement exerting member, which displaces the container, induces a force, or both displaces the container and induces a force.

9. A process of providing a force, a displacement, or both a force and a displacement, comprising:
   a. providing a displaceable container (101) with a heating element capable of exerting force/displacement (135) of sufficient size to contact ends of the container;
   b. providing said heating element which is capable of expanding upon heating and contracting upon cooling, inside said container;
   c. providing electrical insulation (131) for placement inside said container which is capable of electrically insulating said heating element;
   d. providing said heating element comprising a material which heats when electric current flows through said heating element; and
   e. heating said element, which in turn expands element, which in turn causes application of a force by the container, a displacement of the container, or both a force by and a displacement of the container.

10. A process of providing a force, a displacement, or both a force and a displacement, comprising;
    a. providing a displaceable container (101) with a heating element capable of exerting force/displacement (135) of sufficient size to contact ends of the container and which is capable of expansion upon heating or contraction upon cooling;
    b. providing said heating element comprising a material which expands on heating and contracts on cooling and which contains fluid lines (133) which allow fluid to pass through the element for the purpose of changing the temperature of the element; and
    c. heating or cooling said element, which in turn expands or contracts, which in turn causes application of a force by the container, a displacement of the container, or both a force by and a displacement of the container.

11. A process according to 8, 9, or 10 wherein the displacement of the container is achieved by controlling the displacement of the container as a function of at least one key variable such as temperature inside the container, container temperature, or element temperature.

12. A process according to 8, 9, or 10 wherein the force is applied by heating the solid material inside the container, which results in application of force to a specimen, component, or system to which the container is attached, and controlling the force as a function of at least one key variable such as temperature inside the container, container temperature, or element temperature.

13. A process according to 8, 9 or 10, wherein the container (101) is attached to mechanical behavior characterization specimens or to miniaturized mechanical behavior test specimens.

14. A process according to 13, wherein the mechanical behavior specimens or miniaturized mechanical behavior specimens are double cantilever beam specimens, tensile specimens, fracture toughness specimens, creep specimens, fatigue specimens, notched three point bend specimens, or stress relaxation specimens.

15. A process according to 8, 9, or 10 wherein the container (101) force, displacement, or force and displacement as a function of at least one key variable such as element temperature is determined by placing the container within a calibrated conventional mechanical property test machine, heating the element under conditions which simulate those of the intended use of the invention, recording at least one key variable such as element temperature and the test machine force and displacement over a range of forces and displacements, and determining the correlation between at least one key variable such as element temperature and the measured test machine forces and displacements.

16. A process according to 8, 9, or 10 wherein the element is a solid material with a large thermal expansion coefficient.

17. A process according to 8, 9, or 10 wherein the element is a solid material with a large thermal expansion coefficient, the container is a bellows or any otherwise displaceable container, the container contents are comprised of a thermal insulating material or vacuum, and the force and displacement is produced by heating the element, which in turn expands, and during the expansion, the element pushes on the container.

18. A process according to 8, wherein the container is a uniaxial bellows, the element is a solid cylinder with resistance heater wires attached, and the container is evacuated, or contains thermal insulation, or both.

The following references are incorporated herein:
(1) M. F. Kanninen, "An Augmented Double Cantilever Beam Model for Studying Crack Propagation and Arrest", International Journal of Fracture, Vol. 9, No. 1, p. 83 (1973).
(2) Patent SU 1345-095-A, "Soil Testing Instrument Loading Device", Yu. A. Avetikyan, S. A. Akinfiyev, and L. G. Kushnir

I claim:

1. An apparatus for testing an attached specimen by providing a force, a displacement, or both a force and a displacement to load the specimen, the apparatus comprising:
   a. a displaceable container (101) with a heating element (137) capable of heating a force/displacement exerting member (105) and said element of solid material of sufficient size to contact ends of the container;
   b. said solid material force/displacement exerting member, which is capable of expanding upon heating and contracting upon cooling, being located inside said container;
   c. said heating element comprising electrical resistance wire (132) inside electrical insulation (131); and
   d. means for heating said element which in turn heats said force/displacement exerting member, which results in an expansion of the force/displacement exerting member, which displaces the container ends and thereby displaces the tested specimen, induces a force on the tested specimen, or both displaces the container and induces a force on the tested specimen.

2. An apparatus for testing an attached specimen by providing a force, a displacement, or both a force and a displacement to load the specimen, the apparatus comprising:
   a. a displaceable container (101) with a heating element capable of exerting force/displacement (135) and said element of sufficient size to contact ends of the container;
   b. said heating element, which is capable of expanding upon heating and contracting upon cooling, being located inside said container;
   c. electrical insulation (131) inside said container which is capable of electrically insulating said heating element;

d. said heating element comprising a material which heats when elected current flows through said heating element; and e. means for heating said element which in turn expands element, which in turn causes application of a force by the container on the tested specimen, a displacement of the container ends which thereby displaces the specimen, or both a force by and a displacement of the container to load the specimen.

3. An apparatus for testing an attached specimen by providing a force, a displacement, or both a force and a displacement to load the specimen, the apparatus comprising:

a. a displaceable container (101) with a heating element capable of exerting force/displacement (135) and said element of sufficient size to contact ends of the container and which is capable of expansion upon heating or contraction upon cooling;

b. said heating element comprising a material which expands on heating and contracts on cooling and which contains fluid lines (133) which allow fluid to pass through the element for the purpose of changing the temperature of the element; and c. means for heating or cooling said element, which in turn expands or contracts, which in turn causes application of a force by the container on the tested specimen, a displacement of the container ends which thereby displaces the tested specimen, or both a force by and a displacement of the container to load the specimen.

4. An apparatus according to claim 1, claim 2, or claim 3 wherein the displaceable container (101) is in the form of a bellows.

5. An apparatus according to claim 1, claim 2, or claim 3 wherein the heating element material has a large coefficient of thermal expansion.

6. An apparatus according to claim 1, wherein the force/displacement exerting member (105) consists of metal, polymer, organic, ceramic, or any other solid material which expands on heating and contract on cooling.

7. An apparatus according to claim 1, claim 2, or claim 3 wherein thermal insulation is provided around the outside of the container, around the inside of the container, or the container is fabricated using a material which resists heat flow, or any combination of insulation arrangements.

8. A process of testing a specimen by providing a force, a displacement, or both a force and a displacement to load the specimen, comprising:

a. providing a displaceable container (101) with a heating element (137) capable of heating a force/displacement exerting member (105) and said element of solid material of sufficient size to contact ends of the container;

b. providing said solid material force/displacement exerting member, which is capable of expanding upon heating and contracting upon cooling, for placement inside said container;

c. providing said heating element comprising electrical resistance wire (132) inside electrical insulation (131); and d. heating said element which in turn heats said force/displacement exerting member, which results in an expansion of the force/displacement exerting member, which displaces the container ends and thereby displaces the tested specimen, induces a force on the tested specimen, or both displaces the container and induces a force on the tested specimen.

9. A process of testing a specimen by providing a force, a displacement, or both a force and a displacement to load the specimen, comprising:

a. providing a displaceable container (101) with a heating element capable of exerting force/displacement (135) and said element of sufficient size to contact ends of the container;

b. providing said heating element, which is capable of expanding upon heating and contracting upon cooling, inside said container;

c. providing electrical insulation (131) for placement inside said container which is capable of electrically insulating said heating element; and d. providing said heating element comprising a material which heats when electric current flows through said heating element; and e. heating said element, which in turn expands element, which in turn causes application of a force by the container on the tested specimen, a displacement of the container ends which thereby displace the specimen, or both a force by and a displacement of the container to load the specimen.

10. A process of testing a specimen by providing a force, a displacement, or both a force and a displacement to load the specimen, comprising;

a. providing a displaceable container (101) with a heating element capable of exerting force/displacement (135) and said element of sufficient size to contact ends of the container and which is capable of expansion upon heating or contraction upon cooling;

b. providing said heating element comprising a material which expands on heating and contracts on cooling and which contains fluid lines (133) which allow fluid to pass through the element for the purpose of changing the temperature of the element; and c. heating or cooling said element, which in turn expands or contracts, which in turn causes application of a force by the container on the tested specimen, a displacement of the container ends which thereby displaces the tested specimen, or both a force by and a displacement of the container to load the specimen.

11. A process according to claim 8, claim 9, or claim 10 wherein the displacement of the container is achieved by controlling the displacement of the container as a function of at least one key variable including temperature inside the container, container temperature, or element temperature.

12. A process according to claim 8, claim 9, or claim 10 wherein the force is applied by heating the solid material inside the container, which results in application of force to the specimen to which the container is attached, and controlling the force as a function of at least one key variable including temperature inside the container, container temperature, or element temperature.

13. A process according to claim 8, claim 9, or claim 10 wherein the container (101) is attached to mechanical behavior characterization specimens or to miniaturized mechanical behavior test specimens.

14. A process according to claim 13, wherein the mechanical behavior specimens or miniaturized mechanical behavior specimens are double cantilever beam specimens, tensile specimens, fracture toughness specimens, creep specimens, fatigue specimens, notched three point bend specimens, or stress relaxation specimens.

15. A process according to claim 8, claim 9, or claim 10 wherein the container (101) force, displacement, or force and displacement as a function of at least one key variable including element temperature is determined by placing the container within a calibrated conventional mechanical property test machine, heating the element under conditions which simulate those of the intended use of the process, recording the at least one key variable including element temperature and the test machine force and displacement over a range of forces and displacements, and determining the correlation between the at least one key variable and the recorded test machine forces and displacements.

16. A process according to claim 8, claim 9, or claim 10 wherein the element is a solid material with a large thermal expansion coefficient.

17. A process according to claim 8, claim 9 or claim 10, wherein the element is a solid material with a large thermal expansion coefficient, the container is a bellows or any otherwise displaceable container, the container contents are comprised of a thermal insulating material or vacuum, and the force and displacement is produced by heating the element, which in turn expands, and during the expansion, the element pushes on the container.

18. A process according to claim 8, wherein the container is a uniaxial bellows, the element is a solid cylinder with resistance heater wires attached, and the container is evacuated, contains thermal insulation, or both.

* * * * *